US00PP31182P2

(12) United States Plant Patent
Heuger

(10) Patent No.: US PP31,182 P2
(45) Date of Patent: Dec. 3, 2019

(54) ***HELLEBORUS* PLANT NAMED 'COSEH 4800'**

(50) Latin Name: ***Helleborus* x *ericsmithi* X *Helleborus* x *hybridus***
Varietal Denomination: 'COSEH 4800'

(71) Applicant: Josef Heuger, Glandorf (DE)

(72) Inventor: Josef Heuger, Glandorf (DE)

( * ) Notice: Subject to any disclaimer, the term of this patent is extended or adjusted under 35 U.S.C. 154(b) by 0 days.

(21) Appl. No.: 16/350,424

(22) Filed: Nov. 15, 2018

(51) Int. Cl.
*A01H 5/02* (2018.01)
*A01H 6/72* (2018.01)

(52) U.S. Cl.
USPC ..... Plt./439

(58) Field of Classification Search
USPC ..... Plt./439
CPC ..... A01H 5/02; A01H 6/72
See application file for complete search history.

(56) References Cited

PUBLICATIONS

PLUTO Plant Variety Database Jun. 4, 2019. p. 1.*

* cited by examiner

*Primary Examiner* — Annette H Para
(74) *Attorney, Agent, or Firm* — C. A. Whealy

(57) ABSTRACT

A new and distinct cultivar of *Helleborus* plant named 'COSEH 4800', characterized by its relatively tall, upright and mounded plant habit; moderately vigorous growth habit; dark green-colored leaves; moderately freely flowering habit; single greyed purple-colored flowers; and good garden performance.

2 Drawing Sheets

Botanical designation: *Helleborus* x *ericsmithii* X *Helleborus* x *hybridus*.
Cultivar denomination: 'COSEH 4800'.

BACKGROUND OF THE INVENTION

The present invention relates to a new and distinct cultivar of *Helleborus* plant, botanically known as *Helleborus* x *ericsmithii* X *Helleborus* x *hybridus* and hereinafter referred to by the name 'COSEH 4800'.

The new *Helleborus* plant is a product of a planned breeding program conducted by the Inventor in Glandorf, Germany. The objective of the breeding program was to create new uniform *Helleborus* plants with unique and attractive plant habit, leaf and flower coloration and tolerance to biotic and abiotic stress.

The new *Helleborus* plant originated from a cross-pollination conducted by the Inventor in Glandorf, Germany in December, 2012 of a unnamed selection of *Helleborus* x *ericsmithii*, not patented, as the female, or seed patent and an unnamed selection of *Helleborus* x *hybridus*, not patented, as the male, or pollen parent. The new *Helleborus* plant was discovered and selected by the Inventor as a single flowering plant from within the progeny of the stated cross-pollination grown in a controlled greenhouse environment in Glandorf, Germany in November, 2014.

Asexual reproduction of the new *Helleborus* plant by divisions in a controlled environment in Glandorf, Germany since March, 2015 has shown that the unique features of this new *Helleborus* plant are stable and reproduced true to type in successive generations.

SUMMARY OF THE INVENTION

Plants of the new *Helleborus* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'COSEH 4800'. These characteristics in combination distinguish 'COSEH 4800' as a new and distinct *Helleborus* plant:

1. Relatively tall, upright and mounded plant habit.
2. Moderately vigorous growth habit.
3. Dark green-colored leaves.
4. Moderately freely flowering habit.
5. Single greyed purple-colored flowers.
6. Good garden performance.

Plants of the new *Helleborus* differ from plants of the female parent selection in the following characteristics:

1. Plants of the new *Helleborus* are taller than plants of the female parent selection.
2. Plants of the new *Helleborus* have greyed purple-colored flowers whereas plants of the female parent selection have cream-colored flowers.

Plants of the new *Helleborus* differ from plants of the male parent selection in the following characteristics:

1. Plants of the new *Helleborus* are taller than plants of the male parent selection.
2. Plants of the new *Helleborus* have darker greyed purple-colored flowers than plants of the male parent selection.

Plants of the new *Helleborus* can be compared to plants of *Helleborus* x *hybridus* 'Annas Red', not patented. In side-by-side comparisons, plants of the new *Helleborus* differ primarily from plants of 'Annas Red' in the following characteristics:

1. Plants of the new *Helleborus* have less distinct leaf venation than plants of 'Annas Red'.

2. Plants of the new *Helleborus* are more freely flowering than plants of 'Annas Red'.
3. Plants of the new *Helleborus* flower earlier than plants of 'Annas Red'.

BRIEF DESCRIPTION OF THE PHOTOGRAPHS

The accompanying colored photographs illustrate the overall appearance of the new *Helleborus* plant showing the colors as true as it is reasonably possible to obtain in colored reproductions of this type. Colors in the photographs may differ slightly from the color values cited in the detailed botanical description which accurately describe the colors of the new *Helleborus* plant.

The photograph on the first sheet is a side perspective view of a typical flowering plant of 'COSEH 4800' grown in a container.

The photograph on the second sheet is a close-up view of typical flowers of 'COSEH 4800'.

DETAILED BOTANICAL DESCRIPTION

The aforementioned photographs and following observations, measurements and values describe plants grown during November in 17-cm containers in a glass-covered greenhouse in Glandorf, Germany and under cultural practices typical of commercial *Helleborus* production. During the production of the plants, day temperatures ranged from 12° C. to 32° C. and night temperatures ranged from 3° C. to 18° C. Plants were 16 months old when the photographs and the description were taken. In the following description, color references are made to The Royal Horticultural Society Colour Chart, 2015 Edition, except where general terms of ordinary dictionary significance are used.

Botanical classification: *Helleborus* x *ericsmithii* X *Helleborus* x *hybridus* 'COSEH 4800'.

Parentage:

*Female, or seed, parent*.—Unnamed selection of *Helleborus* x *ericsmithii*, not patented.

*Male, or pollen, parent*.—Unnamed selection of *Helleborus* x *hybridus*, not patented.

Propagation:

*Type*.—In vitro meristem culture.

*Time to initiate roots, winter*.—About 50 days at temperatures about 12° C.

*Time to produce a rooted young plant, winter*.—About six months at temperatures ranging from 4° C. to 15° C.

*Root description*.—Thick to thin, fleshy; typically white to brown in color, actual color of the roots is dependent on substrate composition, water quality, fertilizer type and formulation, substrate temperature and physiological age of roots.

*Rooting habit*.—Low branching; sparse.

Plant description:

*Plant and growth habit*.—Herbaceous perennial; relatively tall, upright and mounding plant habit with flowers held within and above the foliar plane; plant shape, roughly flattened globular; moderately vigorous growth habit; moderate growth rate.

*Plant height, soil level to top of foliar plane*.—About 30.3 cm.

*Plant height, soil level to top of flowers*.—About 31.6 cm.

*Plant diameter* (*area of spread*).—About 56 cm.

Leaf description:

*Arrangement*.—Leaves arranged in a basal rosette; leaves palmately compound with typically five leaflets per leaf.

*Leaf length*.—About 20.5 cm.

*Leaf width*.—About 22.5 cm.

*Leaflet length*.—About 14.2 cm.

*Leaflet width*.—About 6.7 cm.

*Leaf shape*.—Palmate; reniform in outline.

*Leaflet shape*.—Obovate to elliptic.

*Leaflet apex*.—Acute to apiculate.

*Leaflet base*.—Attenuate.

*Leaflet margin*.—Coarsely serrate; moderately undulate.

*Leaflet texture and luster, upper surface*.—Smooth, glabrous; leathery; moderately glossy.

*Leaflet texture and luster, lower surface*.—Smooth, glabrous; leathery; slightly glossy.

*Leaflet venation pattern*.—Pinnate.

*Leaflet color*.—Developing leaflets, upper surface: Close to 137C; towards the base, tinged with close to 183A. Developing leaflets, lower surface: Close to between N186C and 200B. Fully developed leaflets, upper surface: Close to darker than between 147A and N189A; venation, close to 143A. Fully developed leaflets, lower surface: Close to 147B; venation, close to 200B.

*Petioles*.—Length: About 20 cm. Diameter: About 6 mm to 8 mm. Strength: Strong. Texture and luster, upper and lower surfaces: Smooth, glabrous; moderately glossy. Color, upper and lower surfaces: Close to 144A; densely covered with small dots, close to 183C.

Flower description:

*Flower shape and habit*.—Single rotate flowers; arranged solitary or in clusters with about 15 flowers each; moderately freely flowering habit with about 27 flowers developing per plant; flowers facing outwardly to nodding.

*Fragrance*.—None detected.

*Natural flowering season*.—Plants begin flowering about ten months after planting; plants flower during the late autumn into the winter in Germany.

*Flower longevity on the plant*.—About ten days; sepals persistent, other flower parts are not persistent.

*Flower buds*.—Length: About 2.4 cm. Diameter: About 1.5 cm. Shape: Broadly ovoid. Texture and luster: Smooth, glabrous; slightly glossy. Color: Close to 195B moderately tinged with close to N77B and 187C; venation, close to N77B and 187C.

*Inflorescence height*.—About 32.4 cm.

*Inflorescence diameter*.—About 18.2 cm.

*Flower diameter*.—About 10.8 cm.

*Flower depth* (*height*).—About 3.3 cm.

*Petals*.—Transformed into nectaries.

*Sepals*.—Quantity and arrangement: About five, arranged in a single whorl. Length: About 5.8 cm. Width: About 4.7 cm. Shape: Broadly ovate to broadly elliptic, slightly concave. Apex: Obtuse. Base: Cuneate. Margin: Entire; moderately to strongly undulate. Texture and luster, upper surface: Smooth, glabrous; matte. Texture and luster, lower surface: Smooth, glabrous; slightly glossy. Color: When opening, upper surface: Close to 59C to 59D; fine dots, close to N186D. When opening, lower surface: Close to N186D; fading slightly towards the margins to close to 187B; venation, close to 187B. Fully opened, upper surface: Close to 186B; fine dots, close to 187B. Fully opened, lower surface: Close to N186D; fading slightly towards the margins to close to 187B; fading towards the apex to close to 186A; venation, close to 187B.

*Flower bracts*.—Quantity per flower: Typically two. Length: About 9 cm. Width: About 4.8 cm. Shape: Ovate.. Apex: Acute. Base: Cuneate. Margin: Distally, serrate; proximally, entire; strongly undulate to nearly crinkled. Color, upper surface: Close to between NN137A and 139A. Color, lower surface: Close to 147B; venation, close to between N186C to 187A.

*Peduncles*.—Length: About 26.1 cm. Diameter: About 0.7 cm to 1 cm. Aspect: About 10° from vertical. Strength: Strong. Texture and luster: Smooth, glabrous; moderately glossy. Color: Close to 144C; fine dots, close to N186D.

*Pedicels*.—Length: About 8.2 cm. Diameter: About 2.5 mm to 3 mm. Aspect: About 20° from peduncle axis. Strength: Moderately strong. Texture and luster: Smooth, glabrous; moderately glossy. Color: Close to 183A; fine dots, close to 195C.

*Reproductive organs*.—Stamens: Quantity per flower: About 100. Filament length: About 1.9 cm. Filament color: Close to 150D. Anther shape: Reniform; basifixed. Anther size: About 2 mm by 3 mm. Anther color: Close to 2C. Pollen amount: Scarce. Pollen color: Close to 4D. Pistils: Quantity per flower: About four to five. Pistil length: About 1.5 cm. Stigma diameter: About 0.3 mm. Stigma shape: Club-shaped. Stigma color: Close to 157D. Style length: About 1.45 cm. Style color: Close to 187B to 187C. Ovary color: Close to 184C; stripes, close to 187C. Nectaries (transformed petals): Quantity per flower: About 16. Length: About 1.3 cm. Diameter: About 3.5 mm. Shape: Tubular, flattened. Texture and luster, inner and outer surfaces: Smooth, glabrous; slightly glossy. Color, immature, inner and outer surfaces: Close to N144B. Color, mature, inner and outer surfaces: Close to N144B; distally, close to 151C; distal color becoming closer to 151B with development.

*Seeds and fruits*.—To date, seed and fruit development have not been observed on plants of the new *Helleborus*.

Garden performance: Plants of the new *Helleborus* have been observed to have good garden performance and to tolerate rain, wind, high temperatures. about 35° C. and to be suitable for USDA Hardiness Zones 5 through 9.

Pathogen & pest resistance: To date, plants of the new *Helleborus* have not been observed to. be resistant to pathogens and pests common to *Helleborus* plants.

It is claimed:

1. A new and distinct *Helleborus* plant named 'COSEH 4800' as illustrated and described.

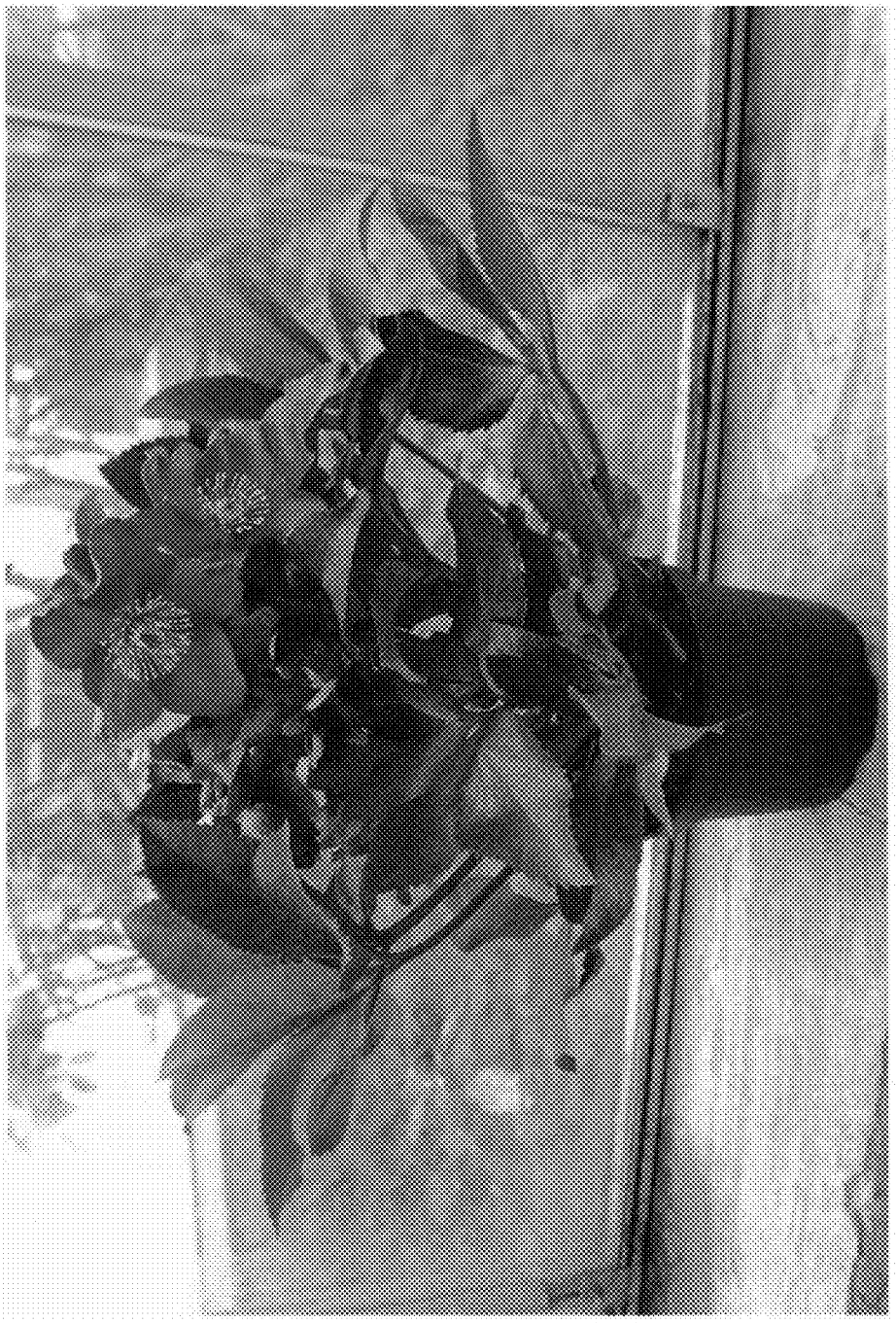

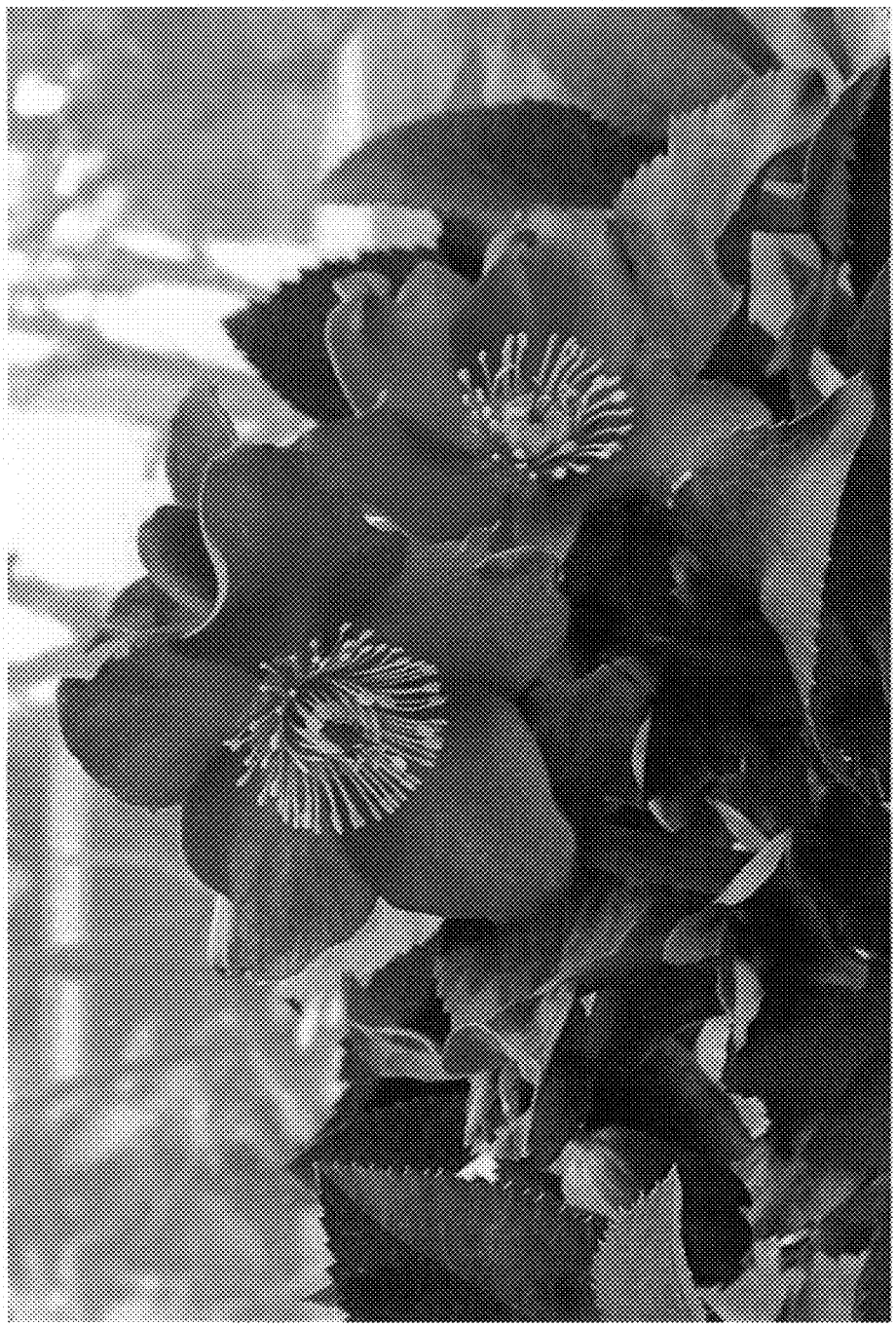

* * * * *